United States Patent [19]

Guy

[11] Patent Number: 5,554,097

[45] Date of Patent: Sep. 10, 1996

[54] SURGICAL INSTRUMENTATION KIT

[75] Inventor: Thomas D. Guy, Fairfield, Conn.

[73] Assignee: United States Surgical Corporation, Norwalk, Conn.

[21] Appl. No.: 317,685

[22] Filed: Oct. 5, 1994

[51] Int. Cl.[6] .................................................. A61B 1/00
[52] U.S. Cl. ........................ 600/102; 600/101; 206/438
[58] Field of Search ................................. 206/363, 366, 206/370, 438; 600/102, 101

[56] References Cited

U.S. PATENT DOCUMENTS

| | | |
|---|---|---|
| 3,579,269 | 5/1971 | Ostensen . |
| 3,592,199 | 7/1971 | Ostensen . |
| 3,739,769 | 6/1973 | Kaye . |
| 4,258,721 | 3/1981 | Parent et al. . |
| 4,546,761 | 10/1985 | McCullough . |
| 4,654,030 | 3/1987 | Moll et al. . |
| 4,823,244 | 4/1989 | Alaybayoglu et al. . |
| 5,109,463 | 4/1992 | Lee .......................................... 385/123 |
| 5,139,478 | 8/1992 | Koninckx et al. ...................... 604/26 |
| 5,149,603 | 9/1992 | Fleming et al. ........................ 429/98 |
| 5,165,387 | 11/1992 | Woodson ................................. 128/6 |
| 5,311,990 | 5/1994 | Kalinski ................................. 206/370 |
| 5,315,985 | 5/1994 | Decarie et al. . |
| 5,335,648 | 8/1994 | Kozawa et al. ......................... 128/6 |
| 5,353,929 | 10/1994 | Foster ................................ 206/438 X |
| 5,392,917 | 2/1995 | Aldern et al. ...................... 206/370 X |

*Primary Examiner*—Richard J. Apley
*Assistant Examiner*—Beverly M. Flanagan

[57] ABSTRACT

A surgical instrumentation kit for preliminary diagnostic endoscopic examination includes a trocar assembly, a self-contained insufflation unit having a supply of insufflation media and a self-contained illuminating unit for supplying illuminating light. The surgical kit is disposable and is intended for use with an endoscope of the type including an optical system and an illumination system. A method for utilizing the kit of the present disclosure is also disclosed.

16 Claims, 8 Drawing Sheets

SURGICAL INSTRUMENTATION KIT

BACKGROUND

1. Technical Field

The technical field is surgical instruments, and, more particularly, surgical kits incorporating surgical instrumentation for performing a preliminary diagnostic endoscopic examination of a patient.

2. Background of Related Art

Emergency diagnostic facilities such as hospital emergency rooms and military triage units require fast and accurate preliminary examinations of incoming patients in order to prioritize the patients' conditions and offer immediate medical care to those facing life-threatening situations. However, in such hospital emergency rooms and military triage units, appropriate diagnostic medical equipment such as x-rays, magnetic resonance imaging, etc. may not be available or may require too much time per patient for any individual patient with critical injuries. Similarly, video screen monitors, computers, light source apparatuses and gas insufflation apparatuses generally are not available due, in part, to the relative expense of these systems and the high number of patients which may be present in the unit at a given time.

Incoming patients in hospital emergency rooms and military triage units frequently have internal injuries to the thoracic or abdominal area of the patient which must be diagnosed to understand the nature and extent of the injuries and immediacy of each patient's need for treatment. X-rays, magnetic resonance imaging and blood tests may require too much time to be performed and provide limited information. Endoscopic or laparoscopic inspection of the thoracic or abdominal cavity may allow medical personnel to rapidly ascertain the nature and seriousness of the patient's condition. However, as noted above, the appropriate diagnostic equipment necessary to perform endoscopic inspection and diagnosis may not always be available. Further, even if the equipment is available, set up of this medical equipment for each individual entails a substantial amount of time. In addition, once the medical equipment is used it must be resterilized for each subsequent use.

Accordingly, the present disclosure is directed to a disposable self-contained surgical instrumentation kit which incorporates the essential medical equipment required to insufflate the abdominal cavity of a patient and perform a preliminary examination of the patient to ascertain the nature and extent of internal injuries to the patient and the immediacy of the need for treatment.

SUMMARY

Generally stated, the present disclosure is directed to a surgical instrumentation kit contemplated for use in, for example, hospital emergency rooms and military triage units, to assist medical personnel in the preliminary diagnostic examination of an incoming patient.

In one embodiment, the surgical instrumentation kit is intended to be used with an endoscope of the type including an optical system for transmitting an image of an object and an illumination system for transferring illuminating light to the area to be viewed. The surgical instrumentation kit includes a trocar assembly including a cannula and an obturator positionable within the cannula, a self contained insufflation unit having a supply of insufflation fluid and being connectable to an insufflation port of the cannula, a self contained illuminating unit for supplying illuminating light to the illumination system of the endoscope and a package having bottom and top covers for accommodating the above noted components.

In an alternative embodiment, the surgical instrumentation kit includes a disposable endoscope which is used in performing the preliminary diagnosis. The disposable endoscope may further include a self-contained illumination unit mounted to the endoscope as supplied to the user in the kit.

The present disclosure is also directed to a novel surgical method for the preliminary diagnosis of a patient using the surgical instrumentation kit of the present disclosure.

The preferred surgical instrumentation kit of the present disclosure incorporates the essential equipment required to perform an accurate preliminary diagnosis of a patient. The kit is made relatively inexpensively and may be completely disposed of after a single use.

BRIEF DESCRIPTION OF THE DRAWINGS

Preferred embodiments are described hereinbelow with reference to the drawings wherein.

DETAILED DESCRIPTION OF THE PREFERRED EMBODIMENTS

Figure 1:
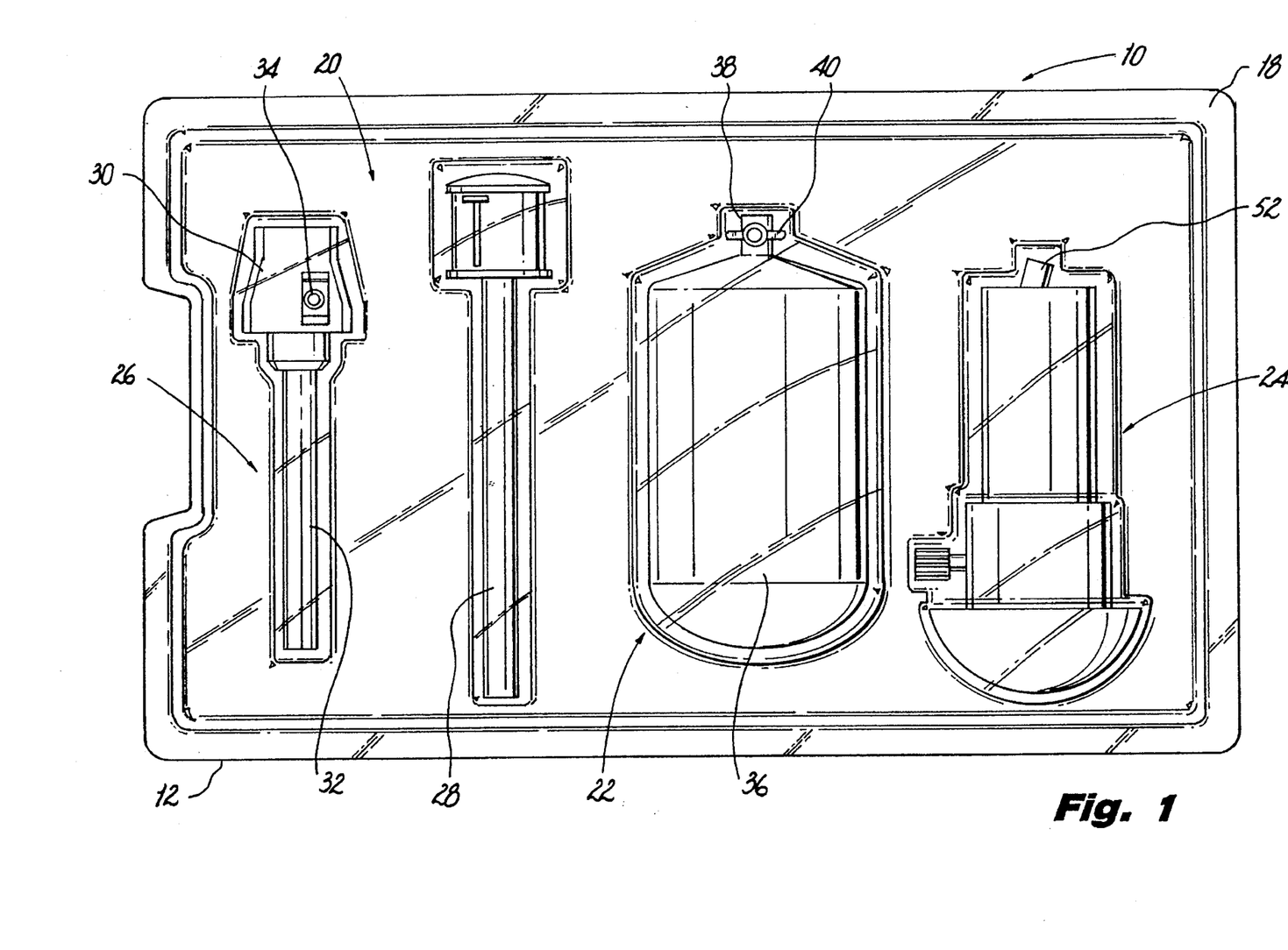
FIG. 1 is a top plan view of the surgical kit for preliminary diagnostic examination constructed in accordance with the principles of the present disclosure.

Referring now in specific detail to the drawings, in which like reference numerals identify similar or identical elements throughout the several views, FIG. 1 illustrates a surgical kit for preliminary diagnostic endoscopic examination. Surgical kit 10 is intended to assist medical personnel in making a preliminary endoscopic diagnosis of a patient and has particular application in hospital emergency rooms, military triage units, etc.

Figure 2:
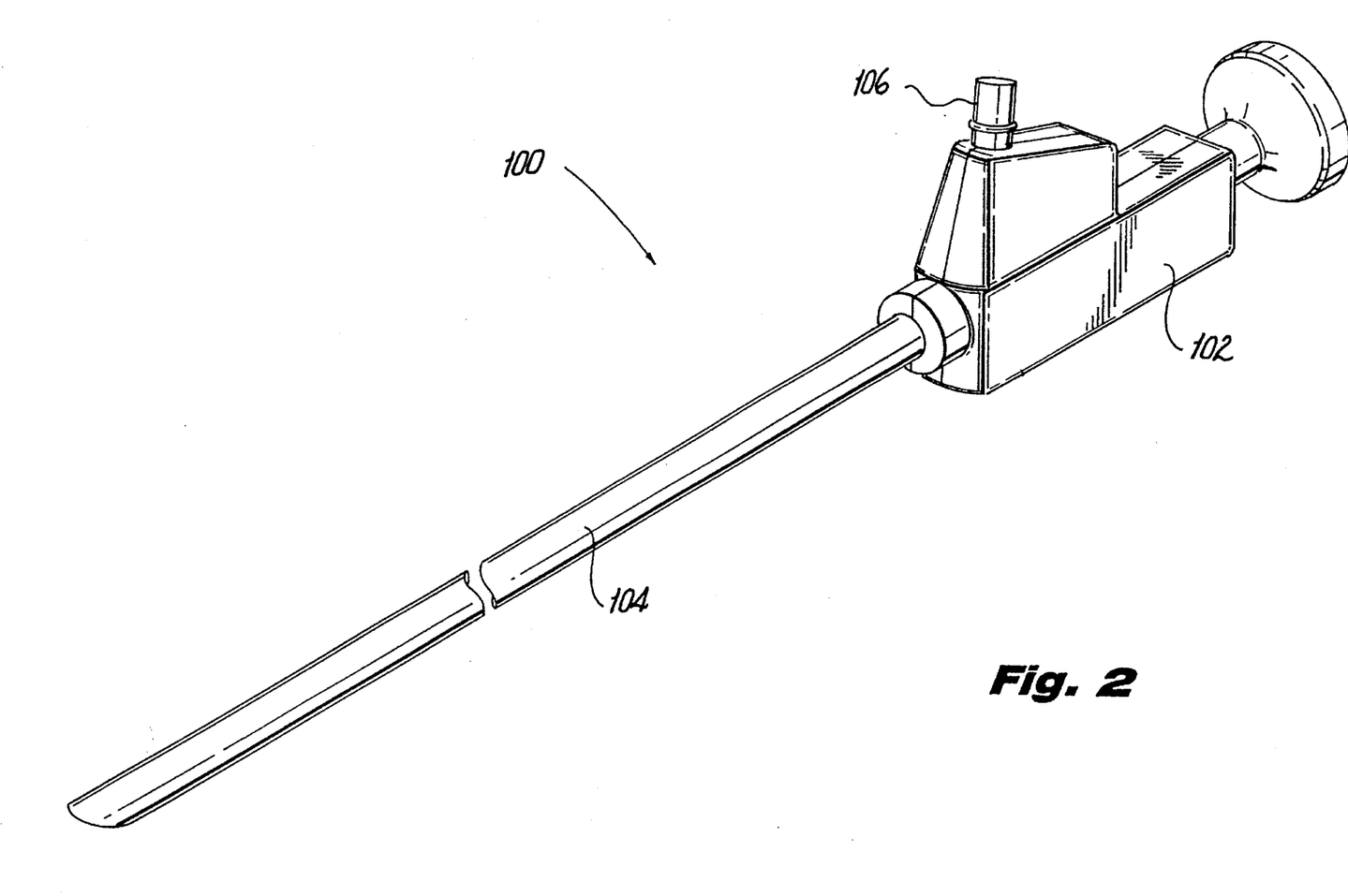
FIG. 2 is a perspective view of an endoscope to be used with the surgical kit of FIG. 1.

Kit 10 is intended for use with an endoscope of the type shown in FIG. 2. This endoscope 100 includes a frame 102 and an endoscopic portion 104 extending distally from the frame 102. Endoscope 100 includes an optical system (not shown) for transferring an image of an object and an illumination system (not shown) for providing illuminating light. Examples of suitable optical systems for endoscopes are disclosed in commonly assigned U.S. Pat. Nos.: 4,964,710 and 5,188,092 and U.S. patent application Ser. Nos.

07/949,212, filed Sep. 11, 1992, 07/985,686, filed Dec. 2, 1992, 08/132,007, filed Oct. 5, 1993 and 08/132,009, filed Oct. 5, 1993, the contents of each being incorporated herein by reference. The illumination system preferably includes a plurality of optical fibers extending the length of endoscopic portion 104 and terminating at illuminating port 106 of frame 102. A suitable endoscope for use with surgical kit 10 of the present disclosure is disclosed in commonly assigned U.S. patent application Ser. No. 08/217,502, filed Mar. 24, 1994, the contents of which are also incorporated by reference. Endoscope 100 may be disposable, limited use or reusable.

Figure 3:
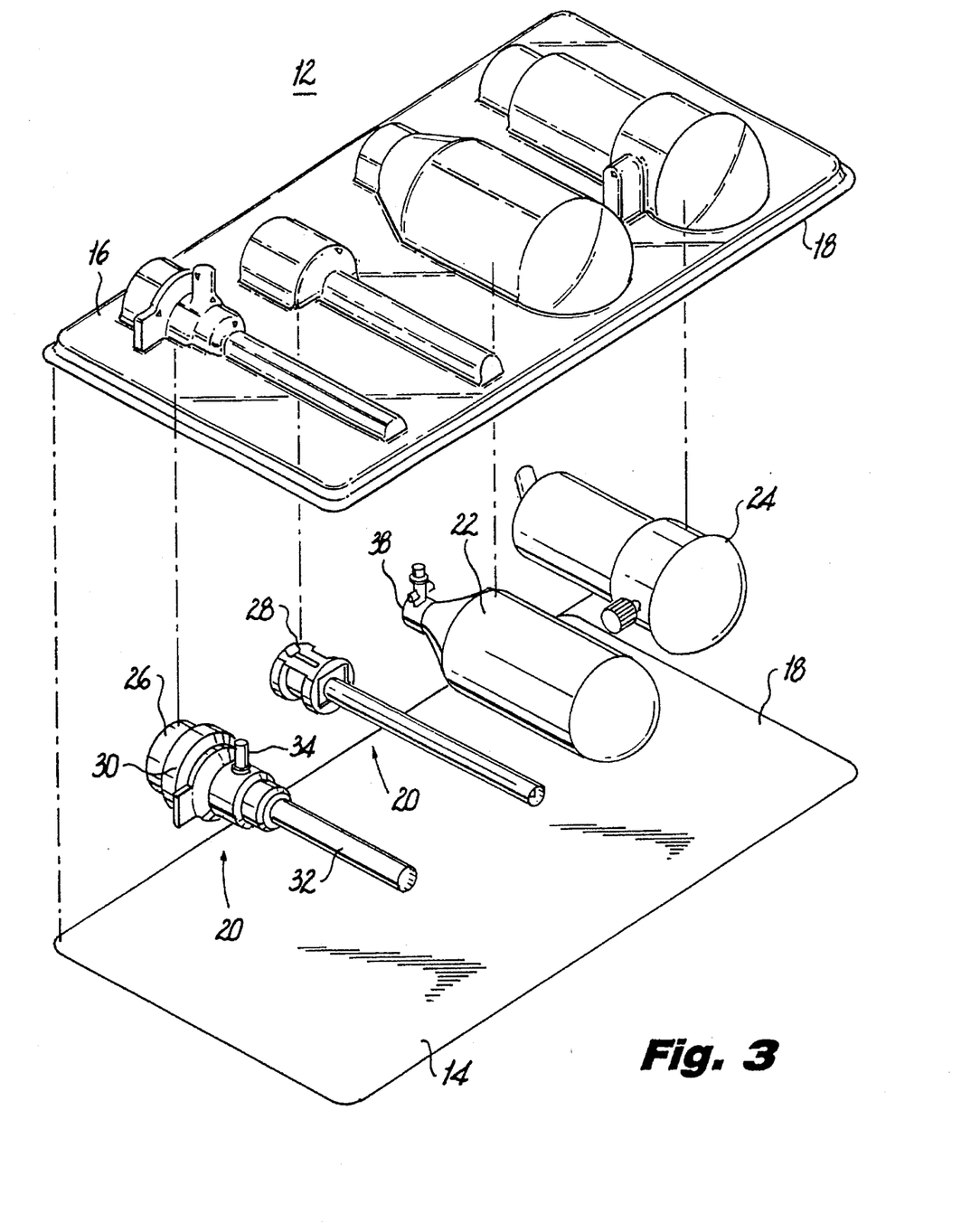
FIG. 3 is an exploded perspective view of the surgical kit of FIG. 1.

Referring now to FIG. 1, in conjunction with FIG. 3, surgical kit 10 includes a package 12 for storing the surgical components contained in the kit. Package 12 includes a bottom panel 14 fabricated from Tyvek™ or the like and a vacuum-formed plastic cover 16 which encloses and displays the instruments within package 12. Tyvek™ is a gas permeable material. Bottom panel 14 also be rigid. Top cover 16 is attached to bottom panel 14 along respective peripheral portions 18 thereof and is preferably transparent to provide an unobstructed view of the instrumentation packaged therein.

Kit 10 includes trocar assembly 20, self-contained insufflation unit 22 and self-contained illuminating unit 24. Trocar assembly 20 includes cannula assembly 26 and obturator assembly 28. Cannula assembly 26 consists of cannula housing 30 and cannula sleeve 32 extending from the housing 30. An insufflation port 34 extends outwardly from cannula housing 30. Insufflation port 34 serves as a conduit for passing insufflation gas through cannula 26 and into the peritoneal cavity. A stop cock valve (not shown) may be connected to insufflation port 34 to enable medical personnel to selectively control the passage of insufflation gases through the cannula. Obturator assembly 28 includes an obturator housing and an obturator portion extending therefrom and insertable into the cannula in a known manner to facilitate insertion of the cannula into the patient. Preferably, the trocar assembly is a disposable safety trocar. Alternatively, the obturator may have a blunt tip. Examples of trocar assemblies which may be used with surgical kit 10 of the present disclosure are described in U.S. Pat. Nos. 5,127,909, 5,104,383, 5,053,016, 4,943,280 and 4,654,030, the contents of each being incorporated herein by reference. Alternatively, the trocar may be an optical trocar. Examples of optical trocars are shown in U.S. Pat. Nos. 5,271,380 and 5,334,150. A preferred optical trocar is disclosed in U.S. patent application Ser. No. 08/249,707, filed May 26, 1994, the contents of which is hereby incorporated by reference.

Figure 4:
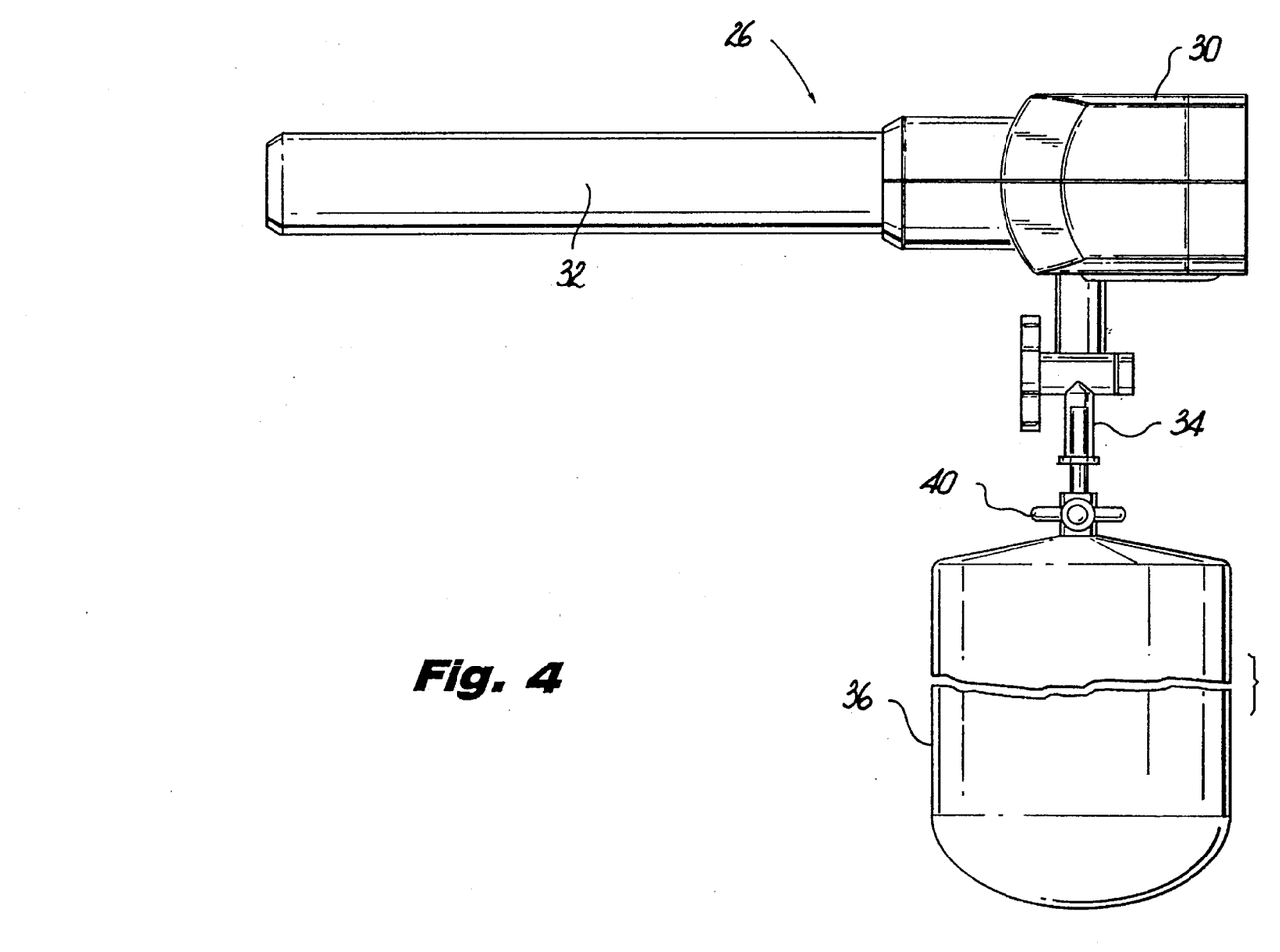
FIG. 4 iS a side plan view of the self contained insufflation unit connected to the cannula of the surgical kit of FIG. 1.

Self-contained insufflation unit 22 includes container 36 which accommodates a supply of insufflation gases, such as $CO_2$, in a liquified state, to inflate the peritoneal cavity. Container 36 includes a connecting portion 38 which is connectable to insufflation port 34 of cannula 26 or a stopcock, depending upon the particular trocar structure to be used. Connecting portion 38 may be in the form of a tube extending from container 36 which is positionable with insufflation port 34 or the stopcock. One skilled in the art may readily determine alternative methods for detachably mounting connecting portion 38 to insufflation port 34 such as with the use of clamps or the like. Insufflation unit 22 may include a pressure reducing valve 40 to selectively dispense the insufflation gas from container 36. FIG. 4 illustrates insufflation unit 22 connected to insufflation port 34 of cannula 26.

Figure 5:
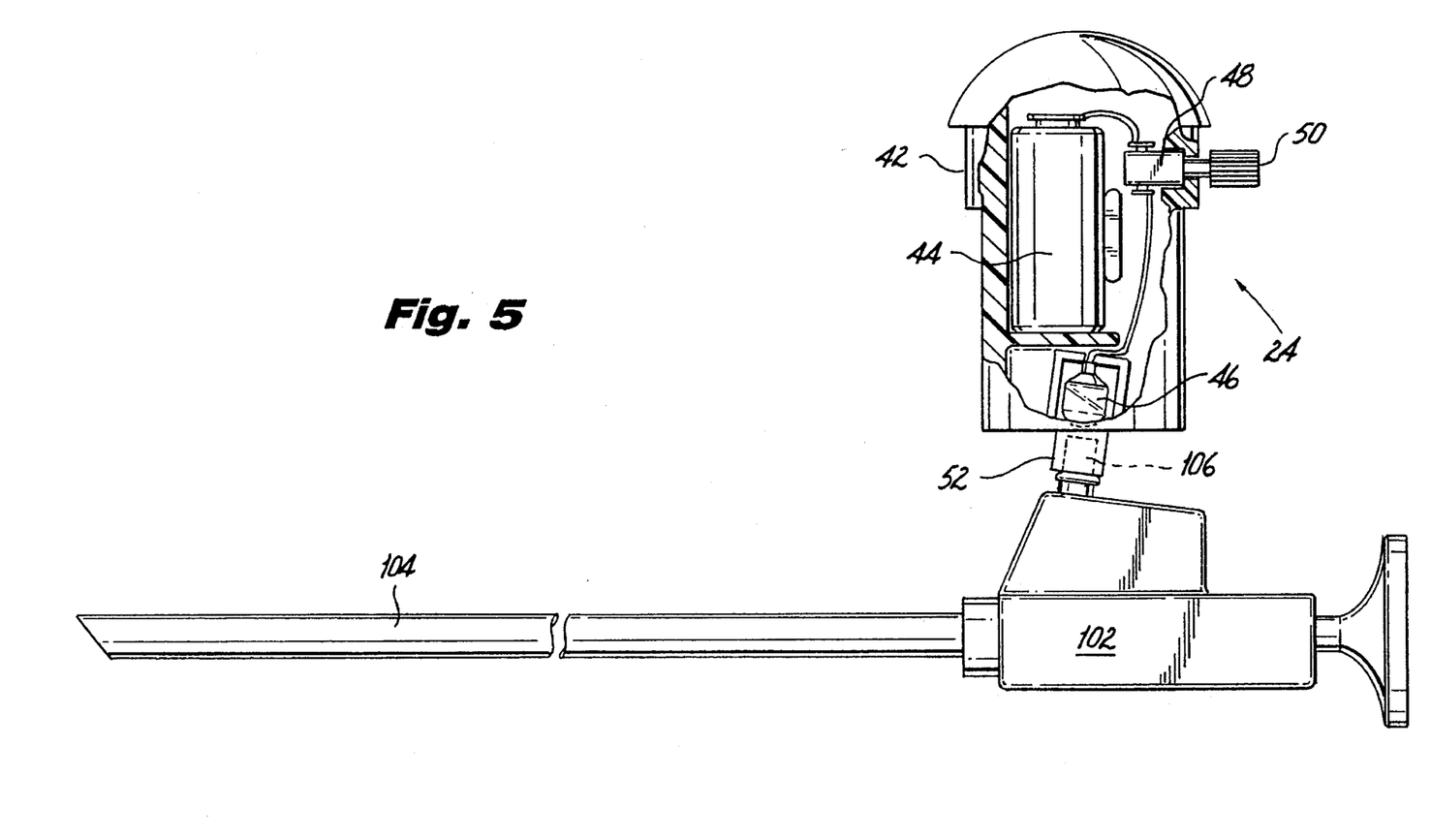
FIG. 5 is a side plan view with portions cut-away of the self contained illuminating unit connected to the illuminating port of a conventional endoscope.

Referring now to FIG. 5, in conjunction with FIG. 1, self-contained illuminating unit 24 will now be described. Illuminating unit 24 includes housing 42 fabricated from a suitable metal or plastic, power source generator 44 and light source 46, each disposed within the housing 40. Power source generator 44 may be any conventional battery capable of providing a sufficient electrical current to illuminate light source 44, including lithium, nickel cadmium batteries, etc. It is contemplated that power source generator 44 may be rechargeable if desired.

Light source 46 is electrically connected to power source generator 44 and is intended to supply illuminating light which is eventually transmitted through the illumination system of an endoscope. Light source 46 may be any conventional high intensity lamp including halogen, mercury vapor, incandescent fluorescent, or an electroluminescent panel, etc. A switch mechanism 48 operated by control knob 50 may be provided to selectively interrupt the current supply from power source generator 44 to light source 46 and/or adjust the intensity of the light.

Illuminating unit 24 is connectable to illuminating port 106 of endoscope 100 via coupler 52 which extends from housing 42. Coupler 52 is preferably configured to be detachably connected to illuminating port 106. In the mounted condition of illuminating unit 24 on endoscope 100, the light generated by light source 46 is directed into the proximal ends of the illuminating fibers of the endoscope 100, which fiber end portions terminate within illuminating port 106 as noted above. It is also contemplated that illuminating unit 24 may include a lens, i.e., a converging lens, to focus the light rays emitted by light source 46 onto the illuminating fibers of the endoscope.

The preferred method of use of surgical kit 10 for preliminary diagnostic examination will now be described. Package 12 is opened and the trocar assembly 20 is removed. The patient is placed in the appropriate position and the trocar assembly 20 is applied against the patient's body until the obturator 28 pierces the peritoneal cavity so as to position cannula sleeve 32 at least partially within the peritoneal cavity. In the alternative, a surgical incision may be made with an appropriate instrument such as a scalpel or the like to form an opening in the peritoneal cavity. Thereafter, the trocar 20 having obturator 28 is forced into the peritoneal cavity through the incision to position the cannula sleeve 32 at least partially within the peritoneal cavity. In accordance with the alternative method, obturator 28 possesses a blunt tip to avoid undesirable piercing of underlying organs. Once cannula sleeve 32 is in the desired position, the obturator 28 is removed from the cannula 26. Insufflation unit 22 is connected to insufflation port 34 of cannula 26 via connecting portion 38 and the self contained gas supply is actuated via pressure relief valve 40 to dispense the $CO_2$ insufflation gases through the cannula and into the peritoneal cavity whereby the peritoneal cavity becomes insufflated and distended.

Figure 6:
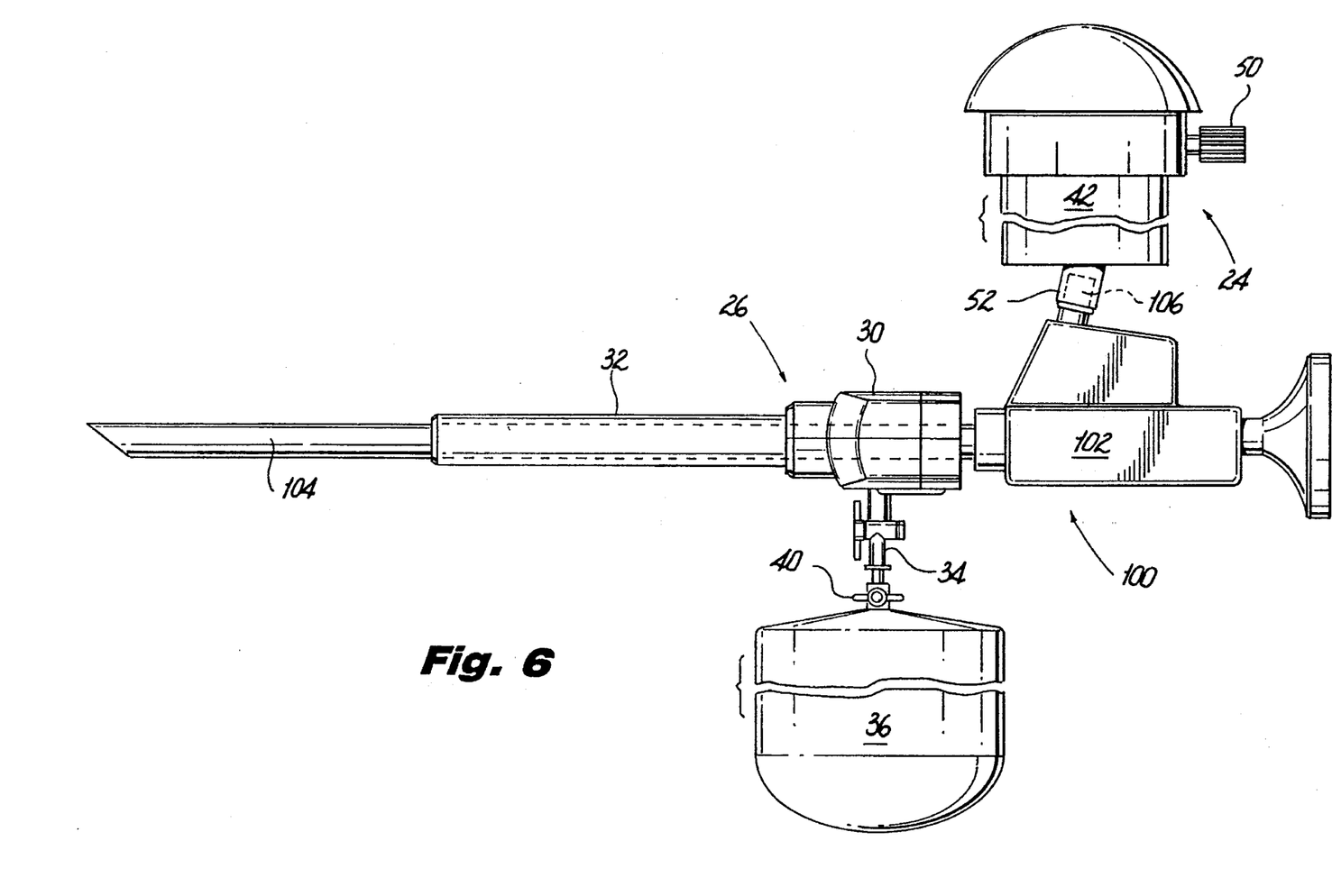
FIG. 6 is a side plan view of the conventional endoscope having the self contained illuminating unit connected thereto positioned within the cannula and with the insufflation unit connected to the cannula.

Referring to FIG. 6, endoscope 100 is then inserted through cannula 26 to extend at least partially within the cavity. Illuminating source 24 is connected to illuminating port 106 of endoscope 100 and the power switch 50 is actuated. Light generated by light source 46 is transferred by the illuminating fiber optics of the endoscope to illuminate the targeted area within the cavity. The surgical personnel thereafter views the cavity via the optical system of the endoscope to formulate a preliminary diagnosis of the patient. Of course, video equipment may be attached to the endoscope, if available.

Figure 7:
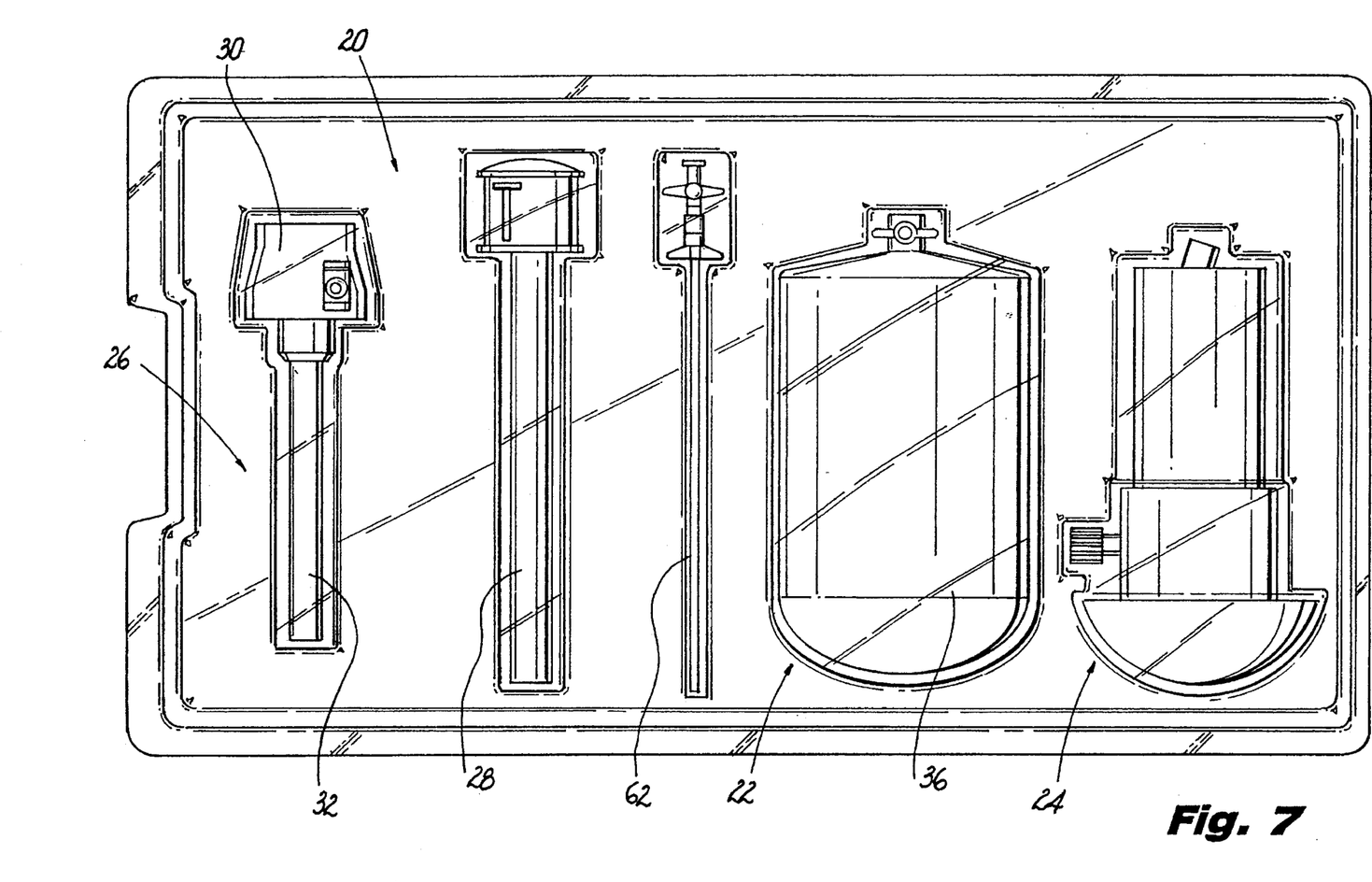
FIG. 7 is a top plan view of an alternative embodiment of the surgical kit of FIG. 1 incorporating a pneumoperitoneum needle.

FIG. 7 illustrates an alternative embodiment. Kit 60 is similar in all respects to kit 10 of FIG. 1, except that kit 60 also includes a pneumoperitoneum needle 62. Pneumoperitoneum needle 62 may be used to initially insufflate the peritoneal cavity prior to insertion of trocar assembly 20. In accordance with this alternative embodiment and method, pneumoperitoneum needle 62 is used to penetrate the peritoneal wall. Thereafter, insufflation unit 22 is connected to the pneumoperitoneum needle 62 and the insufflation unit is actuated to insufflate the peritoneal cavity. Once the peritoneal cavity is insufflated, trocar assembly 20 may be used to penetrate the peritoneal wall with the obturator being thereafter removed leaving cannula 26 at least partially disposed within the peritoneal cavity for subsequent reception of endoscope 100. Insufflation unit 22 may be disconnected from pneumoperitoneum needle 62 and connected to insufflation port 34 of cannula 26 to selectively control the level of insufflation within the peritoneal cavity. A suitable pneumoperitoneum needle which can be incorporated within kit 60 of the present disclosure is described in U.S. Pat. No. 4,808,168, the contents of which are incorporated herein by reference.

Figure 8:
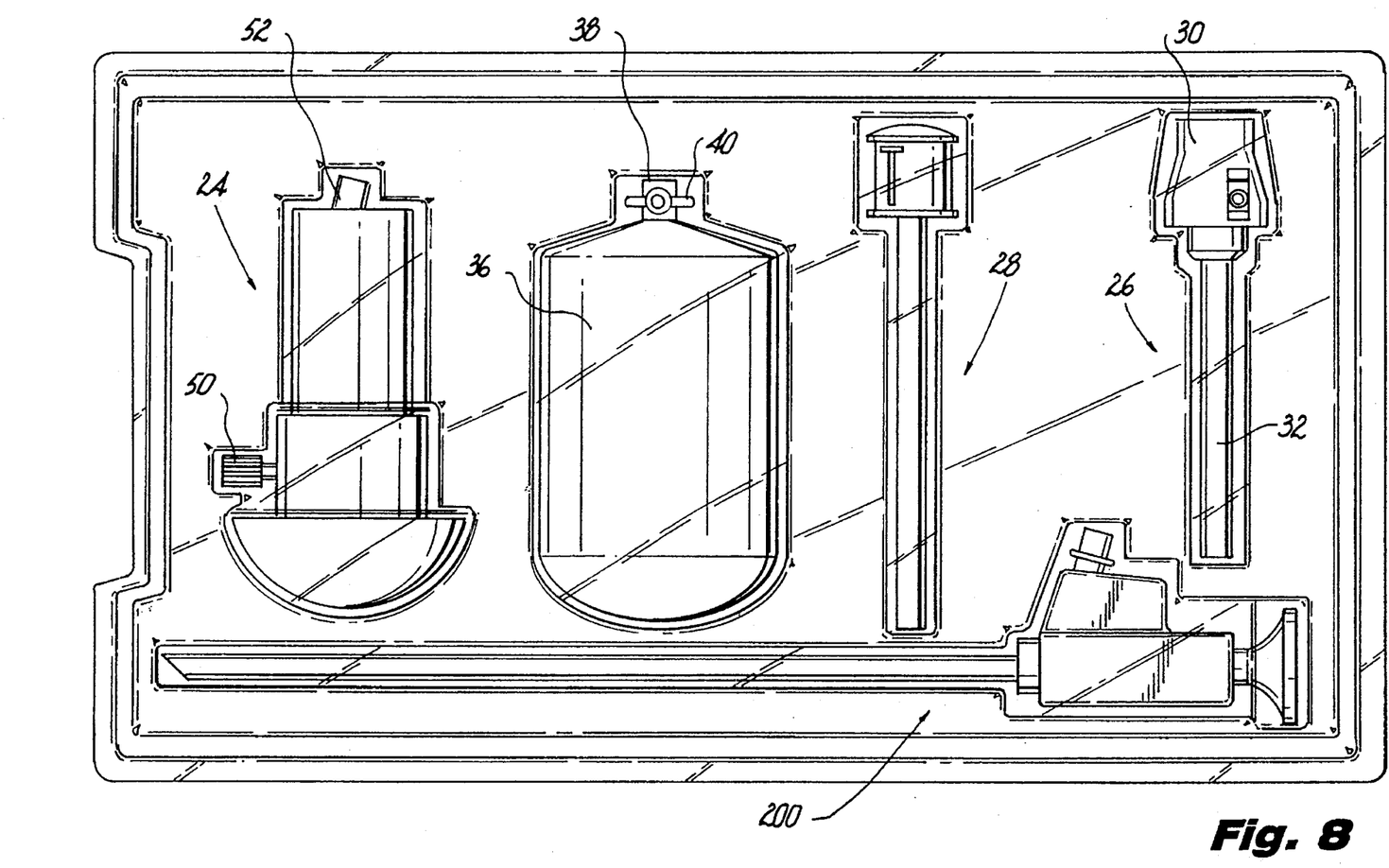
FIG. 8 is a top plan view of another alternative embodiment of the surgical kit of FIG. 1 incorporating an endoscope to be used in the preliminary diagnosis.

FIG. 8 illustrates another alternative embodiment of the surgical kit 10 of the present disclosure. This kit is similar to kit 10 of FIG. 1, but further includes a disposable endoscope 200. U.S. patent application Ser. No. 08/217,502, filed Mar. 24, 1994, the contents of which have been previously incorporated herein by reference describes a disposable endoscope which can be incorporated as part of kit 70. The endoscope described in U.S. patent application Ser. No. 08/217,502 is an inclined angle of view scope and is relatively inexpensive to manufacture. A similar disposable endoscope is described in U.S. Pat. No. 5,341,240. It is also contemplated that the endoscope may be forward-looking rather than angled, particularly where an optical trocar is included in the kit.

The present disclosure provides a surgical kit to perform preliminary diagnostic examination of patients. The components of the kit are relatively inexpensive to manufacture and may be disposed after use.

While the above description contains many specifics, these specifics should not be construed as limitations on the scope of the disclosure, but merely as exemplifications of preferred embodiments thereof. By way of example, a pneumoperitoneum needle may also be incorporated into the kit of FIG. 8. Alternatively, a forward-looking disposable endoscope, optical trocar assembly and pneumoperitoneum needle may all be provided in a kit with a self-contained illumination system and/or a self-contained gas source. Those skilled in the art will envision other possible variations that are within the scope and spirit of the disclosure as defined by the claims appended hereto.

What is claimed is:

1. A surgical kit for diagnostic endoscopic examination using an endoscope including an illuminating port for connection to a light source, the surgical kit comprising:

at least one trocar assembly including a cannula;

at least one self-contained illumination unit configured for engagement with the illuminating port of the endoscope, the illuminating unit including a frame having a connection port configured to engage the illuminating port of the endoscope, a power source generator disposed within the frame for supplying an electrical current, and a light source connected to and energizable by said power source generator; and at least one self-contained insufflator unit having a supply of insufflation media and being connectable to the cannula of the one trocar;

the trocar, the self-contained illuminating unit and the one insufflation unit positioned in a package having a top cover and a bottom cover.

2. The surgical kit of claim 1 wherein said power source generator includes a battery selected from the group consisting of nickel-cadmium and lithium batteries.

3. The surgical kit of claim 1 wherein the light generator includes a lamp selected from the group consisting of fluorescent, incandescent, halogen and mercury vapor lamps.

4. The surgical kit of claim 1 wherein at least a portion of one of the top cover and the bottom cover is formed of a gas permeable material.

5. The surgical kit of claim 1 further comprising a limited use endoscope.

6. A surgical kit for diagnostic endoscopic examination comprising:

a) an endoscope including a frame and an endoscopic portion extending distally from the frame, the endoscope having an optical system for transmitting an image of an object and an illumination system for transferring illuminating light, the endoscope further including an illuminating port for connecting to an external light source;

b) at least one trocar assembly including a cannula having a cannula housing and a cannula sleeve extending from the cannula housing and an obturator positionable within the cannula, the cannula housing including an insufflation port;

c) at least one self-contained insufflation unit dimensioned to contain a supply of insufflation media sufficient to insufflate the abdominal cavity of a patient for preliminary diagnostic examination, the self-contained insufflation unit including an insufflation port configured for engagement with the insufflation port on the cannula housing;

d) at least one self-contained illuminating unit for supplying illuminating light to the illumination system of the endoscope, the illuminating unit including:

i) a frame having a connection port configured to engage the illuminating port of the endoscop;

ii) a power source generator for supplying an electrical current; and iii) a light generator for receiving the electrical current and generating light to be transferred by the illumination system of the endoscope; and e) a package including a bottom cover and a top cover, the package containing the endoscope, the at least one trocar assembly, the at least one self-contained insufflation unit and the at least one self contained illuminating unit.

7. The surgical kit according to claim 6 wherein said power source generator includes a battery selected from the group consisting of nickel-cadmium and lithium batteries.

8. The surgical kit according to claim 6 wherein the connection port of the illuminating unit for connecting to the illuminating port of the endoscope includes a coupler.

9. The surgical kit according to claim 6 wherein the light generator includes a lamp selected from the group consisting of incandescent, fluorescent, halogen and mercury vapor lamps.

10. The surgical kit according to claim 6 wherein the light generator includes an electroluminescent mechanism.

11. The surgical kit according to claim 6 further including a pneumoperitoneum needle.

12. The surgical kit according to claim 1 wherein at least one of the package bottom cover and the package top cover is rigid and at least one of the package top cover and the package bottom cover is transparent for displaying the kit.

13. The surgical kit according to claim 12 wherein the rigid bottom cover is substantially flat and the transparent top cover is a vacuum formed plastic having raised walls generally corresponding in shape to the at least one trocar assembly, the at least one self-contained insufflation unit and the at least one self-contained illuminating unit.

14. The surgical kit according to claim 6 wherein said endoscope is a disposable endoscope not configured for resterilization.

15. A method for performing a preliminary endoscopic diagnostic examination of a patient, comprising the steps of:
   a) providing an endoscope;
   b) providing a surgical kit including an outer package, the outer package having a trocar assembly with a cannula and an obturator positionable within the cannula, a self-contained insufflation unit having a supply of insufflation fluid sufficient to insufflate the abdominal cavity of a patient for preliminary diagnostic examination and a self-contained illuminating unit for supplying illuminating light to the illumination system of the endoscope;
   c) penetrating the peritoneal wall with the trocar assembly such that a portion of the cannula is in communication with the peritoneal cavity;
   d) withdrawing the obturator from the cannula;
   e) connecting the self-contained insufflation unit to an insufflation port of the cannula;
   f) activating the insufflation unit to dispense the insufflation fluid through the cannula and into the peritoneal cavity thereby insufflating the peritoneal cavity;
   g) inserting the endoscope having an optical system for transmitting an image of an object and an illuminating system for transferring illuminating light through the cannula and at least partially into the peritoneal cavity;
   h) connecting the one self-contained illuminating unit to an illuminating port of the endoscope;
   i) activating the self-contained illuminating unit to generate light which is transferred by the illumination system of the endoscope into the peritoneal cavity; and
   j) inspecting the peritoneal cavity through the optical system of the endoscope to formulate a preliminary diagnosis of the patient.

16. A method for performing a preliminary endoscopic diagnostic examination of a patient, comprising the steps of:
   a) providing an endoscope;
   b) providing a surgical kit including a trocar assembly having a cannula and an obturator positionable within the cannula, a pneumoperitoneum needle and a self-contained illuminating unit for supplying illuminating light to the illumination system of the endoscope;
   c) penetrating the peritoneal cavity with the pneumoperitoneum needle;
   d) connecting an insufflation unit to an insufflation port of the pneumoperitoneum needle;
   e) activating the insufflation unit to insufflate the peritoneal cavity;
   f) penetrating the peritoneal wall with the trocar assembly such that a portion of the cannula is in communication with the peritoneal cavity;
   g) withdrawing the obturator from the cannula;
   h) inserting the endoscope having an optical system for transmitting an image of an object and illuminating system for transferring illuminating light through the cannula and at least partially into the peritoneal cavity;
   h) connecting the self-contained illuminating unit to an illuminating port of the endoscope;
   i) activating the self-contained illuminating unit to generate light which is transferred by the illumination system of the endoscope into the peritoneal cavity; and
   j) inspecting the peritoneal cavity through the optical system of the endoscope to formulate a preliminary diagnosis of the patient.

* * * * *